United States Patent
Kuhn et al.

(10) Patent No.: US 7,021,148 B2
(45) Date of Patent: Apr. 4, 2006

(54) APPARATUS AND METHOD FOR SEALING PRESSURE SENSOR MEMBRANES

(75) Inventors: David Kuhn, Lake Bluff, IL (US); Jason Cartwright, Libertyville, IL (US); Ed Chim, Vernon Hills, IL (US); Jan Jensen, Waukegan, IL (US); Michael R. Prisco, Geneva, IL (US); Jerry Ripley, McHenry, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 299 days.

(21) Appl. No.: 10/136,411

(22) Filed: Apr. 30, 2002

(65) Prior Publication Data

US 2003/0200812 A1 Oct. 30, 2003

(51) Int. Cl.
*G01L 7/08* (2006.01)

(52) U.S. Cl. .............................. 73/715; 73/714; 73/723
(58) Field of Classification Search ........... 73/700–756, 73/49.1
See application file for complete search history.

(56) References Cited

U.S. PATENT DOCUMENTS

| | | | |
|---|---|---|---|
| 3,645,139 A | 2/1972 | Zavoda | |
| 3,818,765 A | 6/1974 | Eriksen | |
| 4,064,550 A | 12/1977 | Dias et al. | |
| 4,072,056 A | 2/1978 | Lee | |
| 4,086,815 A | * 5/1978 | Asano et al. | ................. 73/721 |
| 4,109,535 A | 8/1978 | Reed et al. | |
| RE29,867 E | * 12/1978 | Stedman | ....................... 338/2 |
| 4,314,480 A | 2/1982 | Becker | |
| 4,462,409 A | 7/1984 | Pace et al. | |
| 4,499,903 A | 2/1985 | Furst et al. | |
| 4,545,389 A | 10/1985 | Schaberg et al. | |
| 4,562,845 A | 1/1986 | Furst et al. | |
| 4,610,256 A | 9/1986 | Wallace | |
| 4,735,098 A | * 4/1988 | Kavli et al. | ................... 73/718 |
| 4,798,090 A | 1/1989 | Heath et al. | |
| 4,856,339 A | * 8/1989 | Williams | ...................... 73/714 |
| 4,856,340 A | 8/1989 | Garrison | |
| 4,864,463 A | * 9/1989 | Shkedi et al. | ............ 361/283.4 |

(Continued)

FOREIGN PATENT DOCUMENTS

| | | |
|---|---|---|
| DE | 0 685 721 A2 | 12/1995 |
| DE | 0 685 721 B1 | 12/1995 |
| DE | 10032616 A1 | 1/2002 |
| EP | 0 776 469 B1 | 6/1997 |
| JP | 01303155 A2 | 12/1989 |
| JP | 06218047 A2 | 8/1994 |
| JP | 06339526 A2 | 12/1994 |
| WO | WO 97/39679 | 10/1997 |

*Primary Examiner*—Max Noori
*Assistant Examiner*—Jermaine Jenkins
(74) *Attorney, Agent, or Firm*—Joseph P. Reagen; Bell, Boyd & Lloyd LTD

(57) ABSTRACT

The present invention lessens the amount of air entering between mating membranes of a pressure sensor. The pressure sensor of the present invention includes a transducer portion and separate patient or medical fluid transfer portion or dome. The transducer portion is reusable and the dome is disposable. The dome defines a fluid flow chamber that is bounded on one side by a dome membrane. Likewise, the transducer is mounted inside a housing, wherein the housing defines a surface that holds a transducer membrane. The two membranes mate when the dome is fitted onto the transducer housing. The pressure sensor enhances the seal between the mated membranes by creating higher localized contact stresses. The pressure sensor also reduces the amount of gas that permeates from the fluid chamber across the dome membrane and between the interface by making the dome membrane from a material having a low vapor transmission.

28 Claims, 9 Drawing Sheets

U.S. PATENT DOCUMENTS

| | | | |
|---|---|---|---|
| 4,885,983 A | | 12/1989 | Zavoda |
| 4,920,972 A | | 5/1990 | Frank et al. |
| 4,924,701 A | * 5/1990 | Delatorre | ................. 73/152.52 |
| 5,000,049 A | * 3/1991 | Cooper et al. | ................ 73/730 |
| 5,115,724 A | | 5/1992 | Zavoda |
| 5,165,281 A | * 11/1992 | Bell | ............................ 73/718 |
| 5,181,422 A | | 1/1993 | Leonard et al. |
| 5,417,395 A | | 5/1995 | Fowler et al. |
| 5,463,904 A | * 11/1995 | Kalinoski | ................ 73/861.24 |
| 5,483,994 A | | 1/1996 | Maurer |
| 5,501,177 A | * 3/1996 | Edstrom et al. | ........... 119/72.5 |
| 5,540,100 A | | 7/1996 | von Berg |
| 5,551,299 A | | 9/1996 | Tamai et al. |
| 5,551,300 A | | 9/1996 | Vurek et al. |
| 5,614,677 A | | 3/1997 | Wamsiedler et al. |
| 5,644,285 A | | 7/1997 | Maurer |
| 5,752,918 A | | 5/1998 | Fowler et al. |
| 5,848,971 A | | 12/1998 | Fowler et al. |
| 5,868,678 A | | 2/1999 | Brunner et al. |
| 5,892,156 A | | 4/1999 | Kathan et al. |
| 5,914,033 A | | 6/1999 | Carlsson |
| 5,993,395 A | | 11/1999 | Shulze |
| 6,117,086 A | | 9/2000 | Shulze |
| 6,139,503 A | | 10/2000 | Müller |
| 6,168,566 B1 | | 1/2001 | Lia et al. |
| 6,280,406 B1 | | 8/2001 | Dolecek et al. |

\* cited by examiner

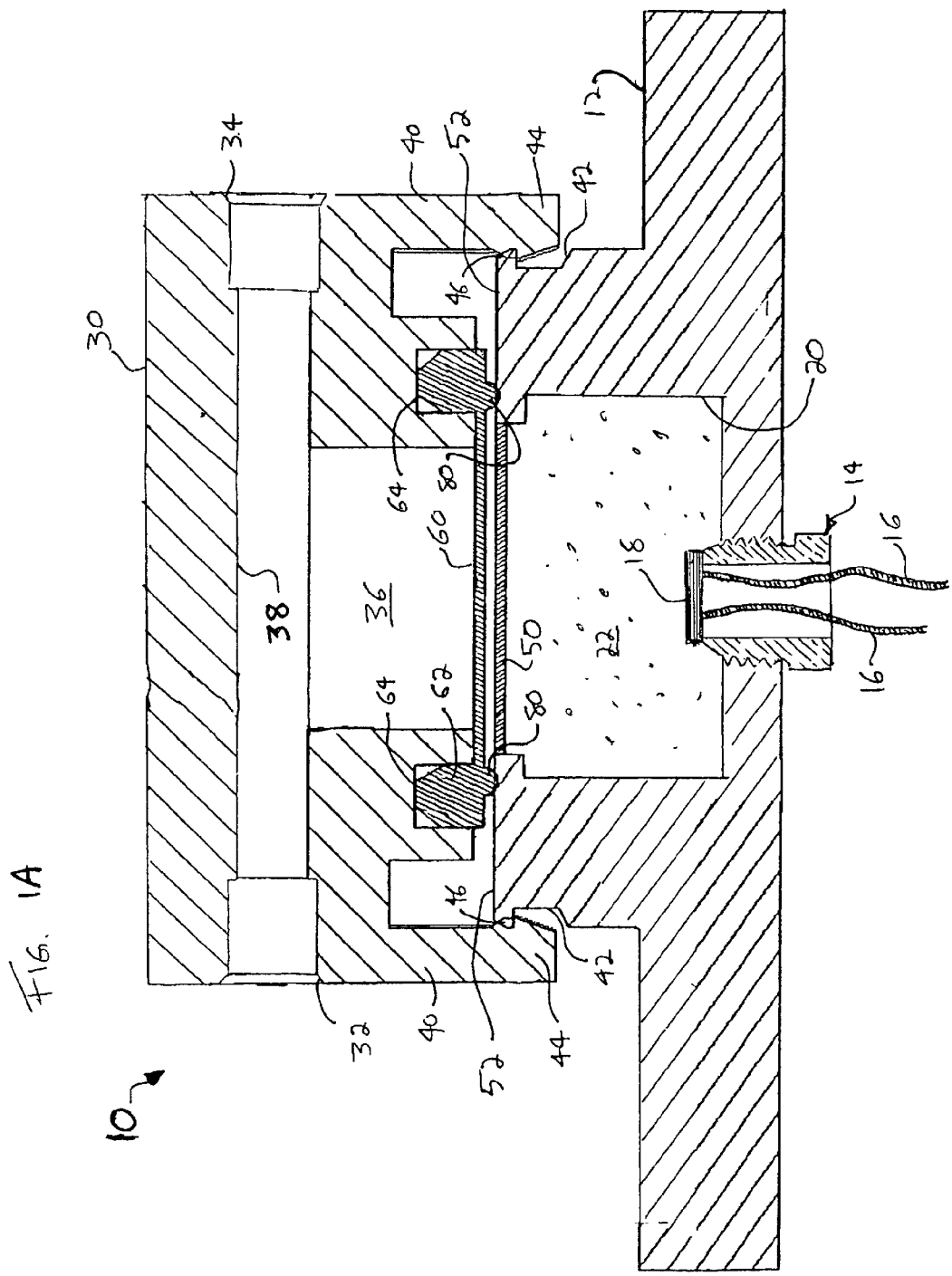

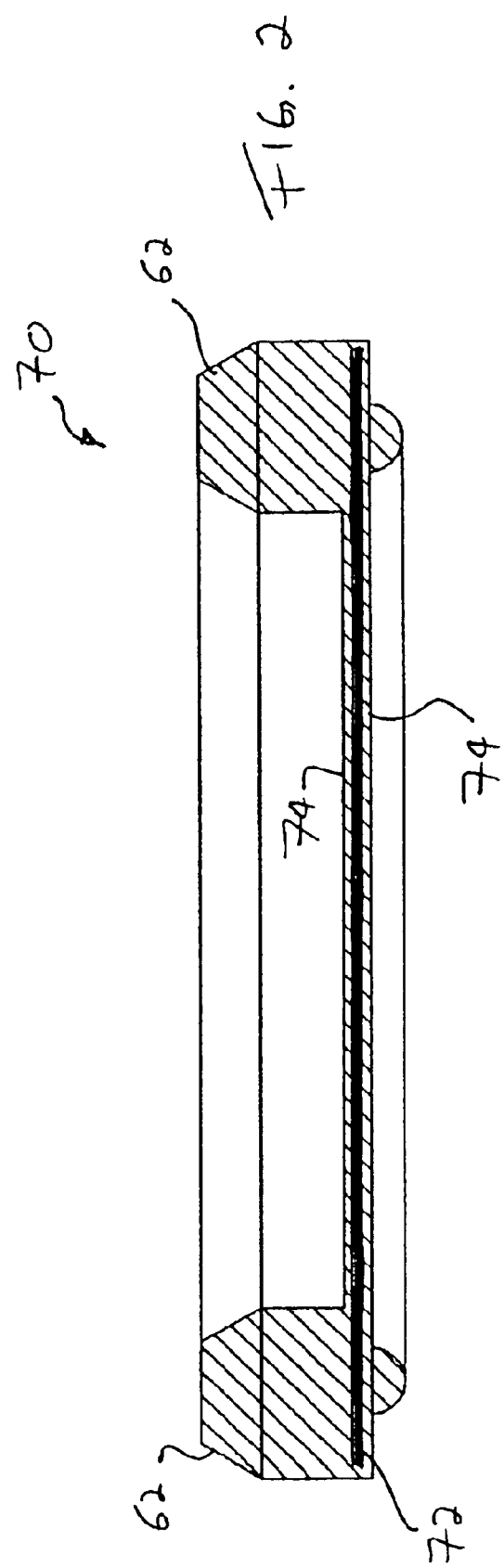

APPARATUS AND METHOD FOR SEALING PRESSURE SENSOR MEMBRANES

BACKGROUND OF THE INVENTION

The present invention relates generally to medical treatments. More specifically, the present invention relates to pressure sensing devices for medical fluids.

Due to disease, insult or injury, a person may require the infusion of a medical fluid. It is known to infuse blood, medicaments, nutrients, replacement solutions, dialysis fluids and other liquids into a patient. It is also known to remove fluid from a patient, for example, during dialysis. Dialysis is used to treat renal system failure, including kidney failure and reduced kidney function.

Renal failure causes several physiological effects. The balance of water, minerals and the excretion of daily metabolic load is no longer possible in renal failure. During renal failure, toxic end products of nitrogen metabolism (urea, creatinine, uric acid, and others) can accumulate in blood and tissues. Dialysis removes waste, toxins and excess water from the body that would otherwise have been removed by normal functioning kidneys.

Hemodialysis and peritoneal dialysis are two types of dialysis therapies commonly used to treat loss of kidney function. Hemodialysis ("HD") treatment utilizes the patient's blood to remove waste, toxins and excess water from the patient. The patient is connected to an HD machine and the patient's blood is pumped through the machine. Catheters are inserted into the patient's veins and arteries to connect the blood flow to and from the HD machine. As blood passes through a dialyzer in the HD machine, the dialyzer removes the waste, toxins and excess water from the patient's blood and returns the blood to infuse back into the patient.

Peritoneal dialysis ("PD") utilizes a dialysis solution or "dialysate", which is infused into a patient's peritoneal cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated on a semi-continuous or continuous basis. There are manual PD techniques, known as Continuous Ambulatory Peritoneal Dialysis ("CAPD"). There are also Automated Peritoneal Dialysis techniques ("APD").

In each type of dialysis treatment, it is critical to know the pressure of the fluid that is being transported to or from the patient. Moreover, in any type of blood transfusion, saline transfusion, or any other type of fluid infusion or flow to or from a patient's body, it is important to know and control the pressure of fluid entering and leaving a patient's body.

Fluid pressure, generally, is sensed using a transducer or strain gauge. Medical fluid transducers have included strain gauges made from a silicon chip. Some medical fluid pressure transducers employ a mechanical linkage to transmit pressure from the fluid to the strain gauge. Many medical transducers, however, have abandoned the mechanical linkage in favor of a hydraulic pressure coupling medium comprised of a silicone elastomer, or "silicone gels". In use, the gel is positioned between the medical fluid (that is sensed for pressure) and the transducer chip, wherein the gel conveys a hydraulic pressure signal to the integral sensing diaphragm of the transducer chip. At the same time, the gel isolates the chip electrically from the medical fluid.

In one type of medical transducer, the entire transducer assembly, including the chip, is discarded after a single use, since the internal components cannot be adequately cleaned for resterilization or reuse. Disposable transducer designs employing semiconductor strain gauge sensors and gel coupling media are desirable because they are rugged and accurate. Further, the disposable transducers do not require attachment of a separate disposable dome as do reusable types of medical pressure transducers.

Regardless of the advantages of the completely disposable medical pressure transducers, manufacturing costs for the pre-calibrated semiconductor chip and associated wiring of these types of transducers remain high. Moreover, the electronics, which could otherwise be reused, are thrown away with the rest of the unit. This is wasteful and costly. Indeed, because the waste contains electronics, it is more costly to dispose.

Accordingly, a pressure sensor that enables the valuable electronics of the transducer to be reused and allows the inexpensive sterile portion for the transfer of the medical fluid to be discarded is desirable. Such pressure sensors exist and typically have a dome portion, which defines a fluid lumen for the medical fluid, and a transducer portion, housing the electronics. The hurdle presented by these types of sensors is in trying to accurately transfer pressure fluctuations in the dome to like fluctuations in the transducer.

In many systems, the medical fluid carrying dome employs a first membrane and the transducer employs a second membrane. The two membranes abut one another and attempt to transmit medical fluid pressure fluctuations through to the strain gauge. One problem with these sensors that employ a membrane to membrane seal is in attempting to maintain the seal along the length of the membranes. A slight amount of air entering even a small part of the interface between the two membranes can falsify readings.

A similar problem exists with materials that have been used for the membranes. In particular, dome membranes can be susceptible to gas diffusion. Certain materials, such as ethylene propylene diene methylene ("EPDM"), have relatively high vapor transmission properties, enabling gas to diffuse from the dome, through the dome membrane, and into the interface between the membranes.

A need therefore exists for a medical fluid pressure sensor having a reusable transducer, a disposable medical fluid dome and an improved and repeatable seal between abutting membranes.

SUMMARY OF THE INVENTION

The present invention relates to medical fluid pressure sensors. More specifically, the present invention provides an apparatus that reduces the amount of air that enters between mating membranes of a pressure sensor. The pressure sensor of the present invention includes a transducer portion and separate patient or medical fluid transfer portion (referred to herein as a "dome" or a "body"). The transducer portion is reusable and the dome is disposable. The dome defines a fluid flow chamber that is bounded on one side by a dome membrane. Likewise, the transducer is mounted inside a housing, wherein the housing defines a surface that holds a transducer membrane.

The transducer can be any type of strain gauge known to those of skill in the art. In an embodiment, the sensor includes a silicone force sensing chip. The transducer membrane in an embodiment is silicone. The dome can hold and allow the transportation of many types of medical fluids such as blood, saline, dialysate (spent or clean), infiltrate, etc. The pressure sensor can likewise be used with many medical treatments, including but not limited to HD, PD, hemofiltration, and any other type of blood transfusion, intravenous transfusion, etc. Accordingly, the pressure sensor can be used with many types of medical devices including dialysis devices. In an embodiment, the reusable transducer housing mounts to the medical or dialysis device, wherein the dome or body removably couples to the housing.

The two membranes mate when the dome is fitted onto the transducer housing. The dome body and transducer housing include mating devices that enable the dome to removably couple to the housing. The pressure sensor enhances the seal between the mated membranes by creating higher localized contact forces or stresses. The pressure sensor also reduces the amount of gas that permeates from the fluid chamber across the dome membrane by making the dome membrane from a material having a low vapor transmission property.

In an embodiment the increased contact forces or stresses are provided by a sealing member or O-ring integral to the dome membrane. The integral sealing member or O-ring of the dome membrane compresses to help prevent air from leaking between the dome and transducer membranes, which mate when the housing and dome are mated. The integral O-ring can have various cross-sectional shapes and in an embodiment is at least partly circular in cross-section. The dome membrane in an embodiment also includes an integral mounting ring that pressure fits into the dome.

In another embodiment, the increased contact forces or stresses are provided by a sealing member or O-ring integral to the dome membrane in combination with a groove defined by the surface of the transducer housing. The surface of the transducer housing surrounds the transducer membrane. In an embodiment, this surface is metal, for example, stainless steel. The integral O-ring of the dome membrane compresses into the groove of the transducer housing when the housing and dome are mated. At the same time, the dome and transducer membranes are mated.

In a further embodiment, the increased contact forces or stresses are provided by a separate O-ring. Here, the O-ring compresses between the dome membrane and the surface of the transducer housing. Like the above embodiment, the surface of the transducer housing surrounds the transducer membrane and defines a groove into which the separate O-ring seats. The separate O-ring compresses into the groove of the transducer housing when the housing and dome are mated. At the same time, the dome and transducer membranes become mated.

In another embodiment, the O-ring compresses between the surface of the transducer housing and a surface of the dome. Here, either one of the surfaces of the transducer housing or the dome defines a groove into which the separate O-ring seats. The separate O-ring compresses into the groove of the transducer or dome surfaces when the housing and dome are mated. At the same time, the dome and transducer membranes become mated.

In yet another embodiment, the increased contact forces or stresses are provided by a raised portion of the surface of the transducer housing, which surrounds the transducer membrane. In an embodiment, this raised portion is metal, for example, stainless steel. The raised portion of the transducer housing compresses into the dome membrane when the housing and dome are mated. At the same time, the dome and transducer membranes become mated.

In any of the above-described embodiments for the increased contact forces, the dome membrane, in one preferred embodiment, is made of a material having a low gas permeability. That is, the dome membrane material has low vapor transmission properties. In an embodiment, the dome membrane includes butyl rubber, which is generally understood to have one of the lowest gas (especially air) permeabilities of all similar materials and is consequently one of the best rubber sealants. In another embodiment, the dome membrane includes a plurality of members or layers. One of the layers is of a material having a low gas permeability, such as a metal foil, a sputter coating of metal or a layer of saran or mylar. The other layer or layers include a flexible and expandable material, such as EPDM, silicone, polyurethane and any combination thereof.

It is therefore an advantage of the present invention to provide a pressure sensor having a reusable transducer.

Another advantage of the present invention is to provide a pressure sensor having a disposable medical or patient fluid transfer portion.

Moreover, an advantage of the present invention is to provide an accurate pressure sensor.

Still another advantage of the present invention is to provide a low cost pressure sensor.

A further advantage of the present invention is to provide a pressure sensor having a relatively gas impermeable membrane.

Yet another advantage of the present invention is to provide a pressure sensor having an additional relatively gas impermeable membrane layer.

Yet a further advantage of the present invention is to provide a pressure sensor having a localized area of high contact force.

Still further, an advantage of the present invention is to provide a pressure sensor having an integral O-ring.

Additionally, it is an advantage of the present invention to provide a pressure sensor having a separate O-ring.

Further still, it is an advantage of the present invention to provide an improved medical infusion device that employs the pressure sensor of the present invention.

Still another advantage of the present invention is to provide an improved dialysis device that employs the pressure sensor of the present invention.

Yet another advantage of the present invention is to provide an improved method of sealing membranes in a medical fluid infusion device.

Additional features and advantages of the present invention are described in, and will be apparent from, the following Detailed Description of the Invention and the Figures.

BRIEF DESCRIPTION OF THE FIGURES

FIG. 1A is a sectioned elevation view of one embodiment of the pressure sensor of the present invention having an integral O-ring that is just about to be compressed.

FIG. 2 is a sectioned elevation view of one embodiment of a dome membrane of the present invention having an additional low gas permeability layer.

DETAILED DESCRIPTION OF THE INVENTION

Figure 1B:
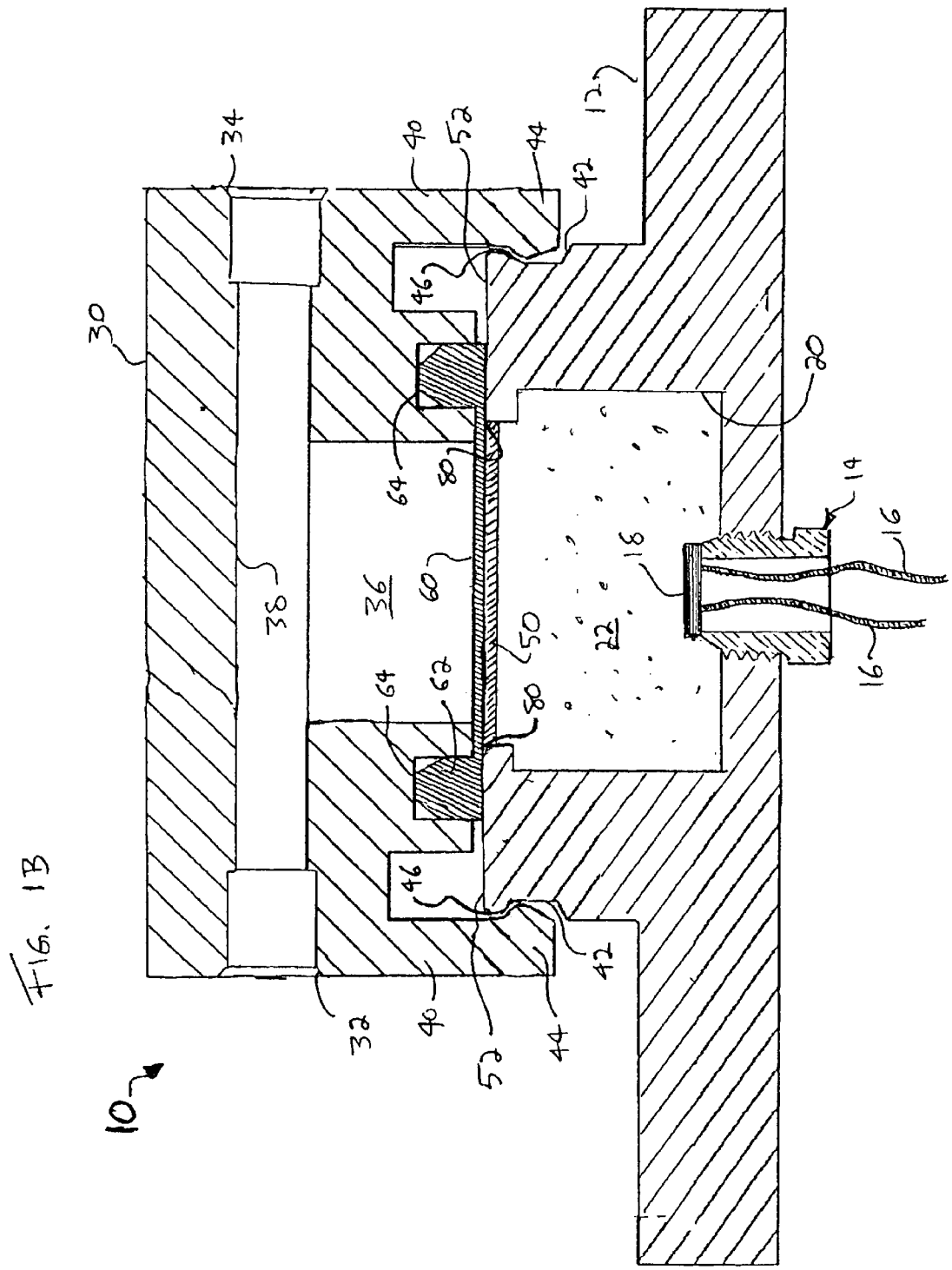
FIG. 1B is the sectioned elevation view of FIG. 1A, wherein the O-ring has been compressed and the pressure sensor is fully sealed.

The present invention provides a pressure sensor and a membrane therefore that helps to prevent air from entering between the membrane and a second membrane when the two membranes are mated. The membranes each belong to a separate component of the pressure sensor, namely, a fluid transfer portion (referred to herein as a "dome" or "body") and a pressure sensing portion (referred to herein as the "transducer housing"). The pressure sensor of the present invention can be used with a variety of fluid transfusion treatments. The pressure sensor is adaptable for use with patient fluids, such as blood, urine, etc. The pressure sensor is adaptable for use with medical fluids, such as saline, dialysate (spent or clean), infiltrate, etc. The pressure sensor can likewise be used with many medical treatments, including but not limited to HD, PD (including CAPD and APD), hemofiltration, and any other type of blood transfusion, intravenous transfusion, etc.

Referring now to the figures, and in particular to FIG. 1A, one embodiment of a pressure sensor 10 is illustrated. Pressure sensor 10 includes a reusable portion or housing 12. The housing 12 can be a separate housing that mounts to a panel or enclosure of a medical device, for example, a dialysis device or machine. The housing 12 is alternatively integral to the housing or enclosure of the medical device or dialysis machine.

The housing 12 holds or supports a transducer 14. In the illustrated embodiment, the transducer 14 threads to the housing 12. The transducer 14 alternatively removably mounts to the housing via fasteners, etc., or permanently mounts to the housing, for example, via a weld.

The transducer 14 includes a number of electrical conductors 16, for example two, three or four conductors, which convey electrical signals to and from a transducer chip 18. The electrical conductors 16 are insulated so that the electrical signals can convey away from the transducer housing 14 to a pressure monitor (elsewhere on the medical or dialysis machine or to a remote device) without risk of shocks, shorts or signal distortion. The chip 18 in an embodiment is a silicone force sensing chip. The housing 12, into which the transducer 14 and chip 18 mount is, in an embodiment, stainless steel.

The transducer housing 12 defines a chamber 20, which in an embodiment holds a pressure transmitting and an electrically and biologically isolating gel, hydraulic fluid or other type of pressure transmission material 22. In an embodiment the pressure transmission material 22 includes silicone. Regardless of the type of pressure transmission material 22 used, the material 22 is responsive to negative or positive pressure signals from the medical fluid flowing through the dome or body. The material 22 transmits the positive or negative pressure signals to the transducer chip 18. In an embodiment, the transducer chip 18 includes a pressure sensing surface, which is exposed to the pressure transmission material 22. Also, in an embodiment, the chip 18 includes on-chip circuitry for predetermined gain and temperature compensation.

A disposable body or dome 30 removably mounts to the transducer housing 12. The disposable body or dome 30 is detached from the reusable transducer housing 12 usually after a single use. The dome 30 defines an inlet fluid port 32, an outlet fluid port 34 and a fluid chamber 36. The illustrated embodiment defines a generally "T" shaped inlet/outlet, wherein the chamber 36 forms the leg of the "T". The dome 30 or body can otherwise define angled or "V" shaped inlets and outlets and/or a contoured chamber. One such dome is disclosed in published PCT application WO 99/37983, entitled, "Connecting Element for Connecting a Transducer With a Sealed Fluid System", the teachings of which are incorporated herein by reference. PCT application WO 99/37983 discloses a dome ceiling, similar to the ceiling 38 of the present invention, which is curved and has a central portion that slopes downward towards the chamber 36 and the membranes.

The body 30 can be constructed from any inert, biologically safe material, such as an inert plastic, for example, a polycarbonate. In an embodiment, the body 30 is clear or transparent. The inlet port 32 and outlet port 34 can include any suitable medical industry interface for connecting to a tube connector or directly to medical fluid tubes. The ports can individually or collectively include a conical packing seat.

The dome or body 30 releasably engages the transducer housing 12. In an embodiment, the body 30 includes a series of tabs 40 that frictionally engage a mating ring 42 defined by the housing 12. When a user presses the body 30 onto the housing 12, the tabs 40 bend slightly outward so that tips 44 of the tabs 40 slide over a rib 46 partially defining the ring 42. Eventually the tips 44 extend far enough over the housing 12, wherein the tips 44 snap into the ring 42. Each of FIGS. 1 and 3 to 6 show the body 30 as it is just about to fully engage the housing 12 (with the tips 44 shown overlapping the rib 46). The body 30 disengages from the housing 12 in the opposite manner, wherein the tabs 40 again bend outwardly, so that the tips 44 slide back over the rib 46 and away from the ring 42.

Both the housing 12 and the body 30 of the pressure sensor 10 include a flexible membrane. The housing 12 includes a membrane 50 disposed over and defining a bounding surface of the chamber 20. The membrane 50 is positioned substantially flush along the top surface (e.g., stainless steel surface) 52 of the housing 12. The transducer membrane 50 is, in an embodiment, silicone of approximately 0.1 to 0.5 mm thickness. Other materials and thicknesses may be used for the transducer membrane 50.

The transducer membrane 50 contacts the dome membrane 60 when the dome 30 and the housing 12 have been mated together. The contacting membranes 50 and 60 enable positive and negative pressure fluctuations of medical or patient fluid in the chamber 36 of the body 30 to be transmitted to the transmission material 22 and to the chip 18. In past pressure sensors, the interface between the contacting membranes 50 and 60 has become corrupted with gas leaking into the interface through the sides of the membranes 50 and 60 and from the medical or patient fluid though a relatively gas permeable dome membrane. The present invention seeks to address both these problems.

First, the dome membrane 60 is made from a substantially gas impermeable material. In a preferred embodiment, the dome membrane 60 is made from butyl rubber or from a blended rubber using butyl, such as halobutyl rubber. Butyl is generally known to have very good sealing properties and to have a very low gas permeability rate. Butyl also has relatively good tear strength, chemical resistance, environmental resistance (including resistance to ozone attack) and is relatively easy to manufacture. The membrane 60 material can be made using a high state of cure (i.e., crosslinic density), wherein the crosslinking reduces the rate of permeation.

Butyl rubber, with respect to air at standard temperature and pressure, is approximately thirty-five times less permeable than ethylene propylene diene methylene ("EPDM"), a known membrane material. Butyl rubber is approximately eighteen times less permeable than natural rubber. Other materials, besides butyl, which have low vapor permeability or transmission rates, and which alone or in combination with butyl rubber or with each other, can be used in the present invention, include neoprene (about 7.5 times less permeable than EPDM), polyurethane (about 6.7 times less permeable than EPDM), Buna-N (Nitrile) (about 7.5 times less permeable than EPDM), Alcryn® (about 25 times less permeable than EPDM), Hypalon® (about 13.5 times less permeable than EPDM), Vamac® (about 19 times less permeable than EPDM), and Viton® (about 19 times less permeable than EPDM).

The membrane 60 also defines a sealing rib 62 that press fits inside of an annular ring 64 defined by the body 30. In an embodiment, sealing rib 62 has an inner radius slightly less than the inner radius of the annular ring 64, so that the membrane 60 has to stretch to fit the rib 62 inside of the ring 64. The sealing rib 62 and the thin portion of the membrane (that engages at least a portion of the membrane 50) are made of the same material in an embodiment, but may be of different materials in other embodiments. The thin, sealing portion of the membrane 60 is, in an embodiment, approximately 0.4 mm thick.

FIG. 1B illustrates the pressure sensor 10 of FIG. 1A, which is now fully sealed. The dome or body 30 is now ready to receive a medical fluid. The dome membrane 60 is flush against the transducer membrane 50. That is, the dome membrane 60 sealingly engages the transducer membrane 50. When the dome membrane 60 moves due to either a positive or negative pressure fluctuation of medical fluid in chamber 36, the transducer membrane 50 follows or moves along with the dome membrane 60. The transducer membrane 50 in turn imparts a positive or negative force on the transmission material 22, which activates the chip 18 of the transducer 14.

Referring now to FIG. 2, another embodiment for making a low vapor permeable dome membrane 70 is illustrated. The dome membrane 70 includes the sealing rib 62 described above. The dome membrane 70 also includes a low vapor transmission layer 72. The low vapor transmission layer 72 can be a layer of metal foil, a sputter coating of metal, saran, mylar and any combination thereof. In another embodiment, the low vapor transmission layer 72 includes butyl rubber, one of the other low vapor transmission materials described above or a film such as SiO2 glass film and EvOH barrier film. In a further embodiment, a low vapor transmission filler is used, such as a reinforcing or lamellar type, which has a plate-like structure that lengthens the diffusion pathway and reduces the rate of permeation.

The low vapor transmission layer 72 in an embodiment is co-extruded with the rest of the membrane 70, so that the layer 72 resides within outer layers 74 of a flexible material, which may also have a low or high vapor transmission rate. The outer layers 74 can include any type of flexible material, for example, EPDM, silicone, polyurethane or any combination of these. In another embodiment, the low permeability layer 72 is bonded to the flexible layer 74 via a suitable adhesive or heat sealing technique.

The low permeability membranes 60 and 70 tend to prevent gas entrained in the medical or patient fluid in the chamber 36 of the dome 30, or present when no medical/patient fluid resides in the chamber 36, from permeating across the dome membrane 60 or 70. Either of the dome membranes 60 and 70 can be used in the embodiments for creating local areas of high contact force, which are about to be presented in FIGS. 1 and 3 to 6. The increased contact forces act to keep gas from entering between the sides of the dome membrane 60 or 70 and the transducer membrane 50.

FIGS. 1A and 1B illustrate one embodiment, wherein the increased contact forces or stresses are provided by an O-ring or sealing member 80, which is formed integrally to the dome membrane 60 or 70. The integral O-ring 80 of the dome membrane 60 or 70 compresses to the top surface (e.g., stainless steel surface) 52 of the housing 12 to help prevent air from leaking between the sides of the dome membrane 60 or 70 and the transducer membrane 50. The integral O-ring 80 compresses enough so that the dome membrane 60 or 70 contacts and seals to the transducer membrane 50. The integral O-ring 80 is co-extruded or co-molded with the remainder of the dome membrane 60 and with at least part of the dome membrane 70.

Figure 3:
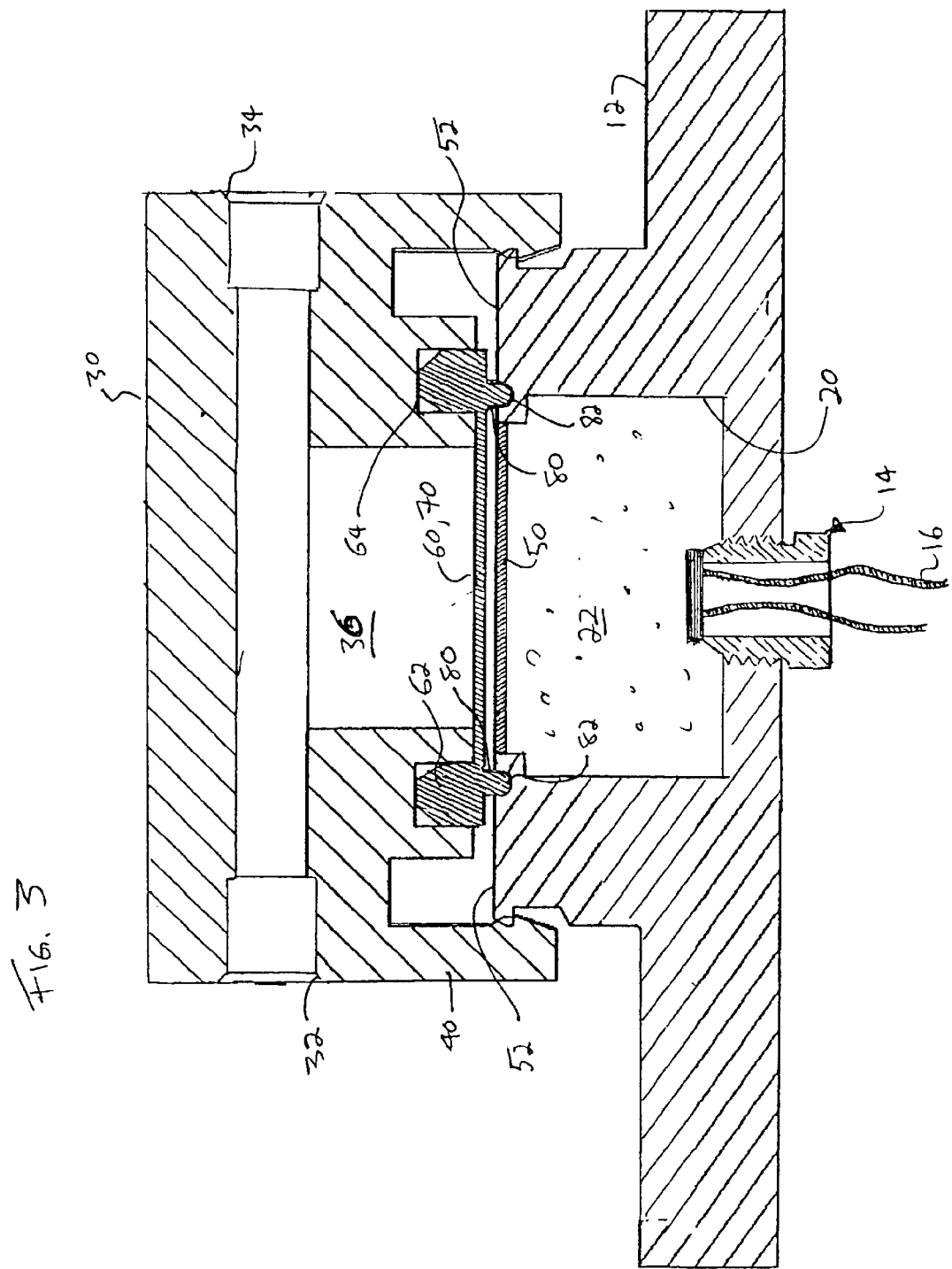
FIG. 3 is a sectioned elevation view of another embodiment of the pressure sensor of the present invention having an integral O-ring and a mating groove.

Referring now to FIG. 3, in another embodiment, the increased contact forces or stresses are provided by the integral O-ring 80 in combination with a groove 82 defined by the surface 52 of the transducer housing 12. The groove 82 is formed to fit the cross-sectional shape of the O-ring 80. The surface 52 of the transducer housing 12 surrounds the transducer membrane 50 and is metal, for example, stainless steel. The integral O-ring 80 of the dome membrane compresses into the groove 82 of the transducer housing 12 when the housing and dome are mated, so as to allow the dome membrane 60 or 70 and transducer membrane 50 to contact and seal to each other.

Figure 4:
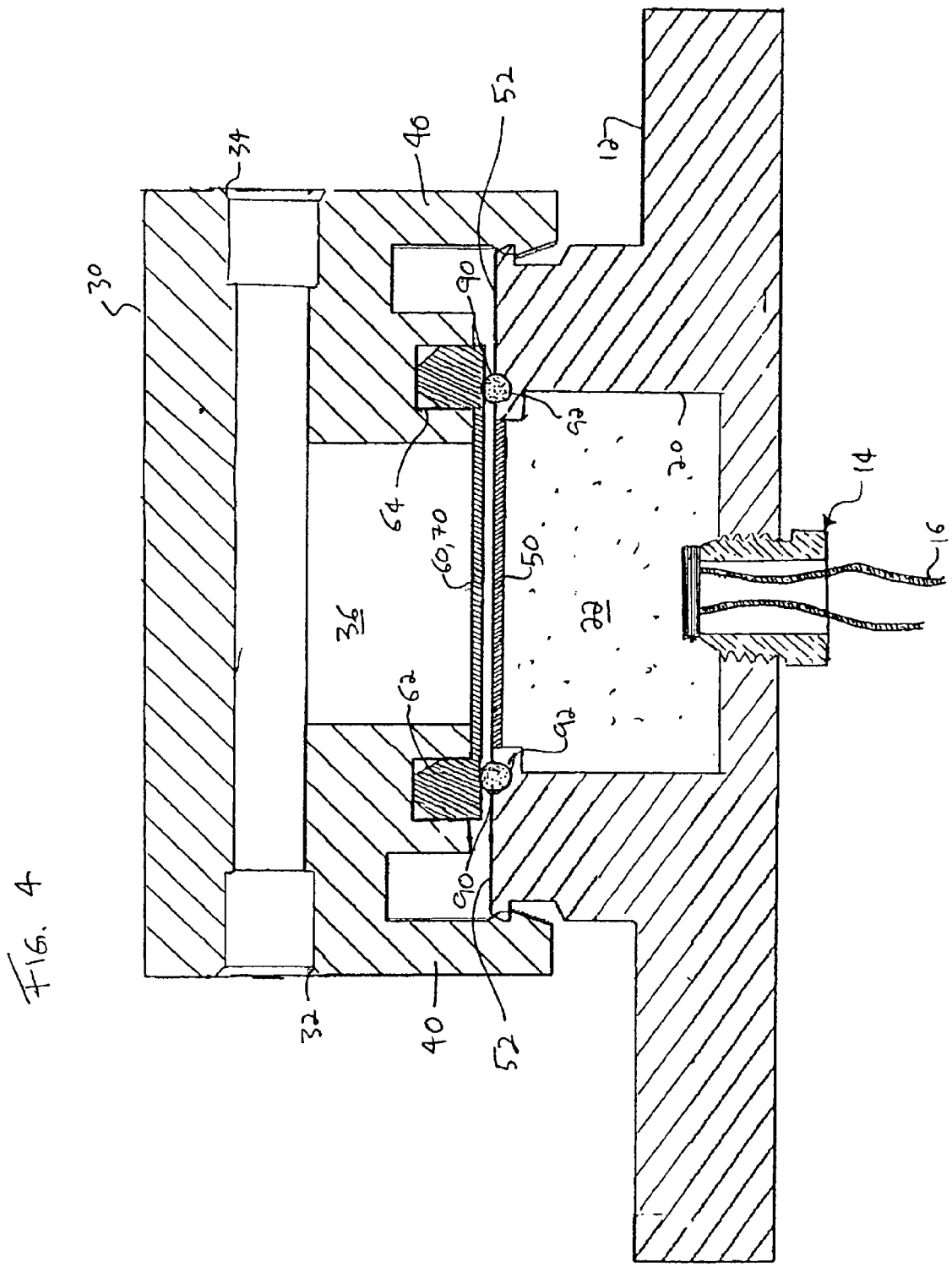
FIG. 4 is a sectioned elevation view of another embodiment of the pressure sensor of the present invention having a separate O-ring and a mating groove.

Referring now to FIG. 4, in a further embodiment, the increased contact forces or stresses are provided by a separate O-ring or sealing member 90. In an embodiment, the O-ring 90 compresses between the dome membrane 60 or 70 and the surface 52 of the transducer housing 12. Here, like the above embodiment, the surface 52 of the transducer housing 12 surrounds the transducer membrane 50 and defines a groove 92 into which the separate O-ring 90 seats. The separate O-ring 90 compresses into the groove 92 of the transducer housing 12 when the housing and dome are mated, so as to allow the dome membrane 60 or 70 and transducer membrane 50 to contact and seal to each other. The separate O-ring 90 can have any of the cross-sectional shapes described below, wherein the groove 92 has a similar shape. The groove 92 in an embodiment also serves to provide a storage place for the separate O-ring 90, during packaging, shipping and set-up. The O-ring 90 therefore slightly pressure fits into the groove 92.

Figure 5:
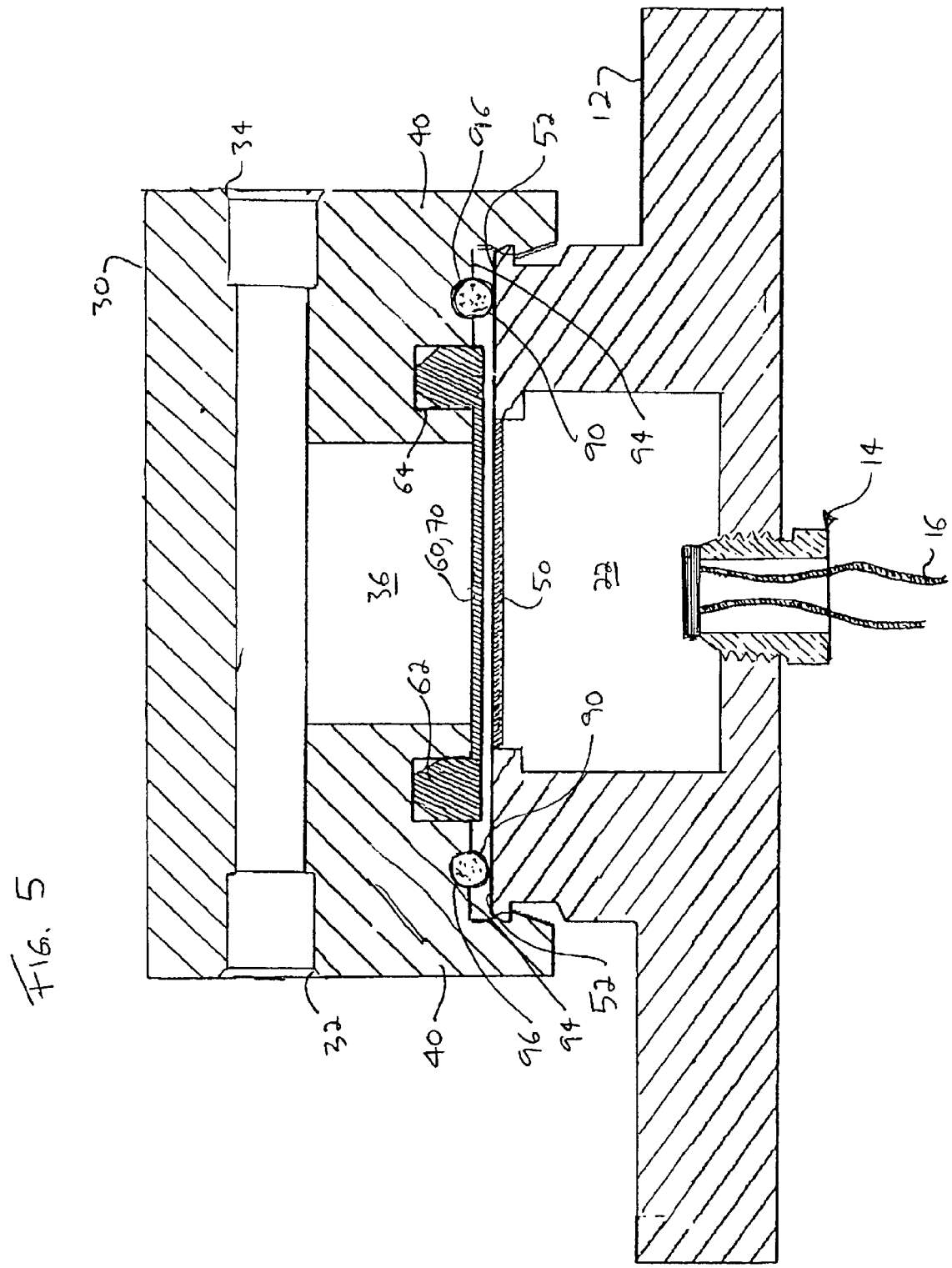
FIG. 5 is a sectioned elevation view of a further embodiment of the pressure sensor of the present invention having a separate O-ring and a mating groove.

Referring now to FIG. 5, in another embodiment, the O-ring or sealing member 90 compresses between the surface 52 of the transducer housing 12 and a surface 94 of the body 30. Here, either one of the surfaces 52 or 94 of the transducer housing 12 or the dome 30, respectively, defines a groove 92 (in surface 52 shown previously in FIG. 4) or 96 (in surface 94) into which the separate O-ring 90 seats and is stored during packaging, shipping and set-up. The separate O-ring 90 compresses into the groove 92 or 96 of the transducer or dome surfaces 52 or 94, respectively, when the housing and dome are mated, so as to allow the dome membrane 60 or 70 and transducer membrane 50 to contact and seal to each other. The separate O-ring 90 can have any of the cross-sectional shapes described below, wherein the groove 92 or 96 has a similar shape.

Figure 6:
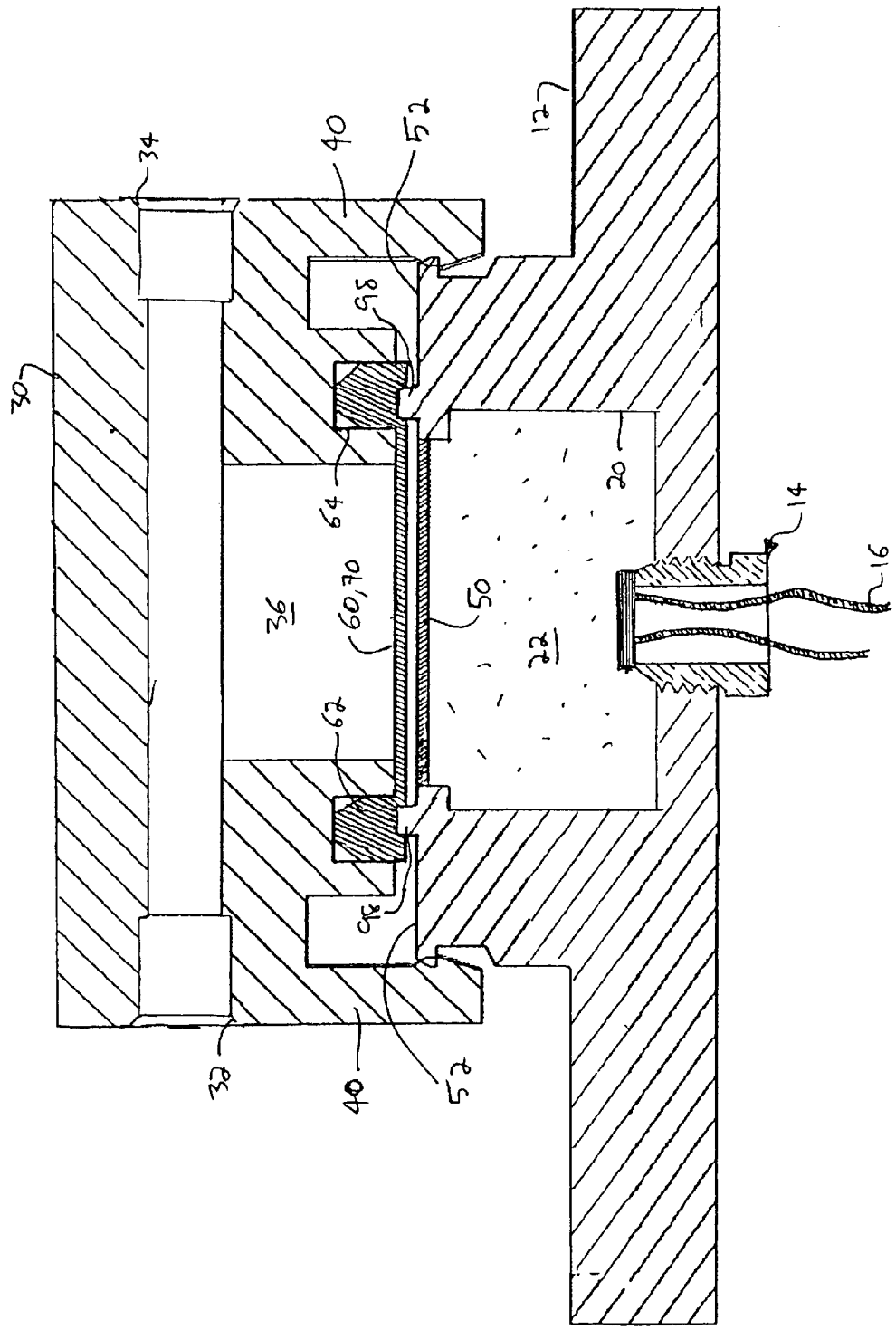
FIG. 6 is a sectioned elevation view of yet another embodiment of the pressure sensor of the present invention having a raised contact force increasing portion.

Referring now to FIG. 6, in yet another embodiment, the increased contact forces or stresses are provided by a raised portion 98 of the surface 52 of the transducer housing 52, which surrounds the transducer membrane 50. In an embodiment, the raised portion 98 is metal, for example, stainless steel. The raised portion 98 of the transducer housing 12 compresses into the dome membrane 60 or 70 at a point where the membrane 60 or 70 is backed up by the sealing rib 62, i.e., where the membrane 60 or 70 has enough material to accept the raised portion 98. The raised portion 98, like the O-rings, can have a variety of cross-sectional shapes, such as rectangular, trapezoidal, circular, etc. The raised portion 98 compresses into the dome membrane 60 or 70 when the housing 12 and dome 30 are mated, so as to allow the dome membrane 60 or 70 and transducer membrane 50 to contact and seal to each other.

Figure 7:
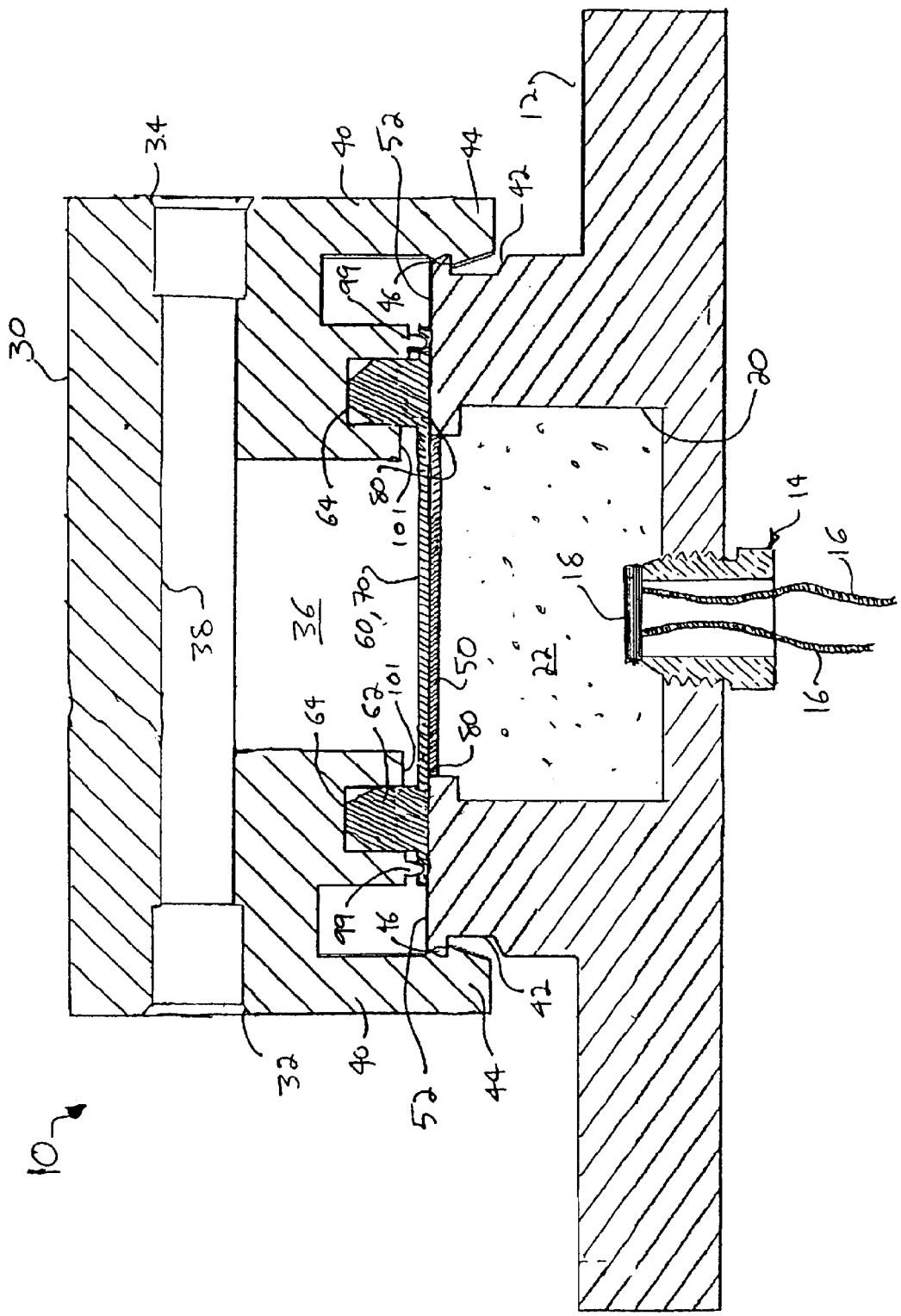
FIG. 7 is a sectioned view of still another embodiment of the pressure sensor of the present invention, wherein the dome body includes a localized contact extension.

Referring now to FIG. 7, yet another embodiment places a raised portion on the dome or body 30 rather than the transducer housing 12 as in FIG. 6. Here, the increased contact forces or stresses are provided by an extension 99 of the surface 101 of the dome 30. In an embodiment, the extension 99 is made of the same material as the dome 30, for example, plastic. The extension 99 of the transducer housing 12 compresses into the dome membrane 60 or 70 at a point where the membrane 60 or 70 thickened as seen in Fig. 7 i.e., where the membrane 60 or 70 has enough material to accept the extension 99.

The extension 99, like the O-rings, can have a variety of cross-sectional shapes, such as rectangular, trapezoidal, circular, etc. As illustrated, the extension 99 compresses into the dome membrane 60 or 70 when the housing 12 and dome 30 are mated, so as to allow the dome membrane 60 or 70 and transducer membrane 50 to contact and seal to each other. Further, the annular ring 64 presses on the sealing rib 62 so that the membrane 60 or 70 also seals generally to the surface 52 of the transducer housing 12.

Figure 8:
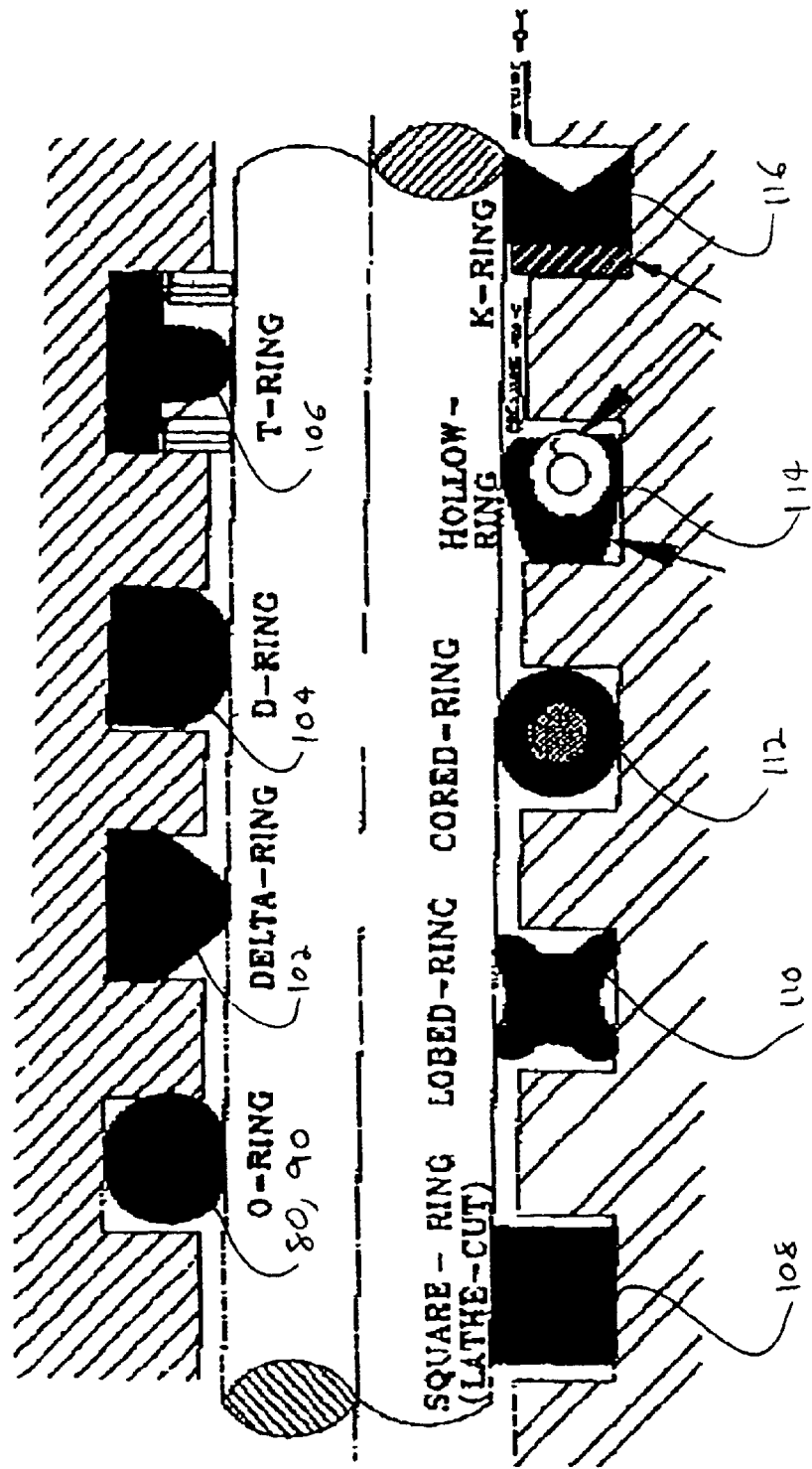
FIG. 8 illustrates various different cross-sectional shapes that the sealing member of the present invention can assume.

Referring now to FIG. 8, any of the sealing members disclosed herein, such as the integral O-ring 80 or the separate O-ring 90, can have at least a partially circular cross-sectional shape as illustrated in FIGS. 1 and 3 to 6. Alternatively, the sealing members can have various partial or full cross-sectional shapes, such as those shapes commonly associated with a delta-ring 102, D-ring 104, T-ring 106, square-ring 108, lobed-ring 110, cored-ring 112, hollow-ring 114 and K-ring 116.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A fluid pressure sensor comprising:
    a housing having a first membrane;
    a transducer positioned inside the housing;
    a body including a fluid inlet and a fluid outlet removably coupled to the housing; and
    a second membrane provided with the body that contacts at least a portion of the first membrane when the body is coupled to the housing, the second membrane including an integral sealing member projecting from the second membrane towards the housing.

2. The fluid pressure sensor of claim 1, wherein the second membrane includes a mounting ring that pressure fits into the body.

3. The fluid pressure sensor of claim 1, wherein the second membrane includes a material selected from the group consisting of butyl rubber, neoprene, polyurethane, Buna-N, saran, mylar, a sputter coating of metal, a metal film and any combination thereof.

4. The fluid pressure sensor of claim 1, wherein the second membrane includes a first member and a second member, the second member having a lower gas permeability than the first member.

5. The fluid pressure sensor of claim 1, wherein the integral sealing member compresses to a surface of the housing that surrounds the first membrane.

6. The fluid pressure sensor of claim 1, wherein the sealing member is selected from the group consisting of: an O-ring, a delta-ring, a D-ring, a T-ring, a square-ring, a lobed-ring, a cored-ring, a hollow-ring and a K-ring.

7. A fluid pressure sensor comprising:
    a housing having a first membrane;
    a transducer positioned inside the housing;
    a body including a fluid inlet and a fluid outlet removably coupled to the housing via a coupling mechanism;
    a second membrane provided with the body that contacts at least a portion of the first membrane when the body is coupled to the housing; and
    an apparatus in addition to the coupling mechanism that creates a localized contact force between the second membrane and a surface of the housing surrounding the first membrane.

8. The fluid pressure sensor of claim 7, wherein the second membrane includes a material selected from the group consisting of butyl rubber, neoprene, polyurethane, Buna-N, saran, mylar, a sputter coating of metal, a metal film and any combination thereof.

9. The fluid pressure sensor of claim 7, wherein the apparatus includes a groove in the surface of the housing and a sealing member integral to the second membrane that compresses into the groove.

10. The fluid pressure sensor of claim 9, wherein the surface of the housing defining the groove is metal.

11. The fluid pressure sensor of claim 7, wherein the apparatus includes a groove in the surface of the housing and a separate sealing member compressed between the second membrane and the groove.

12. The fluid pressure sensor of claim 11, wherein the separate sealing member pressure fits into the groove when the housing and the body are separated.

13. The fluid pressure sensor of claim 7, wherein the apparatus includes a raised portion extending from the surface of the housing contacting the second membrane.

14. The fluid pressure sensor of claim 13, wherein the surface and the raised portion are metal.

15. The fluid pressure sensor of claim 7, wherein the apparatus includes a raised portion extending from a surface of the body.

16. A fluid pressure sensor comprising:
    a housing having a first surface and a first membrane;
    a transducer positioned inside the housing;
    a body including a second surface, a fluid inlet and a fluid outlet removably coupled to the housing; and a second membrane provided with the body that contacts at least a portion of the first membrane when the body is coupled to the housing; and a sealing member positioned between the first surface and the second surfaces.

17. The fluid pressure sensor of claim 16, wherein one of the first and second surfaces defines a groove that houses the sealing member.

18. The fluid pressure sensor of claim 16, wherein the second membrane includes a material selected from the group consisting of butyl rubber, neoprene, polyurethane, Buna-N, saran, mylar, a sputter coating of metal, a metal film and any combination thereof.

19. A fluid pressure sensor comprising:

a housing having a first membrane;

a transducer positioned inside the housing;

a body including a fluid inlet and a fluid outlet removably coupled to the housing; and a second membrane provided with the body that contacts at least a portion of the first membrane when the body is coupled to the housing, the second membrane constructed at least partly of a synthetic and electrically resistive material that is at least five times less permeable to air at standard temperature and pressure than ethylene propylene diene methylene ("EPDM").

20. The fluid pressure sensor of claim 19, wherein the material includes butyl rubber.

21. A fluid pressure sensor comprising:

a housing having a surface surrounding a first membrane;

a transducer positioned inside the housing;

a body including a fluid inlet and a fluid outlet and having a means for removably coupling to the housing; and a second membrane provided with the body that contacts at least a portion of the first membrane when the body is coupled to the housing, the second membrane including a first material and a second material having a lower gas permeability than the first material.

22. The fluid pressure sensor of claim 21, wherein the second material is bonded to first material.

23. The fluid pressure sensor of claim 21, wherein the first material is selected from the group consisting of: ethylene propylene diene methylene (EPDM), silicone, polyurethane and any combination thereof.

24. The fluid pressure sensor of claim 21, wherein the second member includes a material selected from the group consisting of: metal foil, a sputter coating of metal, saran, mylar, SiO$_2$ glass film, EvOH barrier film and any combination thereof.

25. A medical infusion device comprising:

an enclosure; and a pressure sensor mounted to the enclosure, the pressure sensor including
a housing having a first membrane,
a transducer positioned inside the housing,
a body including a fluid inlet and a fluid outlet removably coupled to the housing,
a second membrane provided with the body that contacts at least a portion of the first membrane when the body is coupled to the housing, and
an apparatus that creates a localized contact force between the second membrane and a surface of the housing surrounding the first membrane.

26. The medical infusion device of claim 25, wherein the housing is mounted to the enclosure.

27. A dialysis device comprising:

an enclosure; and a pressure sensor mounted to the enclosure, the pressure sensor including
a housing having a first membrane;
a transducer positioned inside the housing;
a body including a fluid inlet and a fluid outlet removably coupled to the housing, and
a second membrane provided with the body that contacts at least a portion of the first membrane when the body is coupled to the housing, the second membrane constructed at least partly of a synthetic and electrically resistive material that is at least five times less permeable to air at standard temperature and pressure than ethylene propylene diene methylene ("EPDM").

28. The dialysis device of claim 27, wherein the pressure sensor monitors pressure of a fluid selected from the group consisting of: blood, dialysate, infusate, saline and any combination thereof.

* * * * *